United States Patent
Vrancken Peeters (10) Patent No.: US 11,219,450 B2
(45) Date of Patent: Jan. 11, 2022

(54) SURGICAL SUTURE APPARATUS (71) Applicant: Mellon Medical B.V., Nijmegen (NL)

(72) Inventor: Mark-Paul Franciscus Maria Vrancken Peeters, Nijmegen (NL)

(73) Assignee: Mellon Medical B.V., Nijmegen (NL)

( * ) Notice: Subject to any disclaimer, the term of this patent is extended or adjusted under 35 U.S.C. 154(b) by 388 days.

(21) Appl. No.: 16/080,042

(22) PCT Filed: Mar. 10, 2017

(86) PCT No.: PCT/NL2017/050152
§ 371 (c)(1),
(2) Date: Aug. 27, 2018

(87) PCT Pub. No.: WO2017/155406
PCT Pub. Date: Sep. 14, 2017

(65) Prior Publication Data
US 2019/0059881 A1 Feb. 28, 2019

(30) Foreign Application Priority Data
Mar. 11, 2016 (NL) .................................... 2016418

(51) Int. Cl.
A61B 17/062 (2006.01)
A61B 17/06 (2006.01)
A61B 17/04 (2006.01)

(52) U.S. Cl.
CPC ........ *A61B 17/062* (2013.01); *A61B 17/0491* (2013.01); *A61B 17/06004* (2013.01);
(Continued)

(58) Field of Classification Search
CPC .......... A61B 17/06066; A61B 17/0491; A61B 17/06004; A61B 17/062; A61B 17/0625;
(Continued)

(56) References Cited

U.S. PATENT DOCUMENTS 3,807,407 A * 4/1974 Schweizer ............. A61B 17/04
606/145
5,571,090 A * 11/1996 Sherts ................ A61B 17/0469
606/139
(Continued)

FOREIGN PATENT DOCUMENTS

| CA | 2537139 A1 | 3/1997 |
| EP | 0647431 A2 | 4/1995 |
| WO | 2013/032329 A1 | 3/2013 |

Primary Examiner — Jing Rui Ou
(74) Attorney, Agent, or Firm — Hoffmann & Baron, LLP (57) ABSTRACT A surgical suture apparatus for passing a double-ended surgical needle forwards and backwards includes a first and second jaw element, and an operating device to operate a first holding device in the first jaw element and a second holding device in the second jaw element to alternately hold a first needle-end by the first holding device and a second needle-end by the second holding device. The first jaw element and second jaw element are movable with respect to each other between a take-over position and an open position. The operating device includes a switch device movable between a first operating position, in which a needle is held by the first holding device, and a second operating position, in which the needle is held by the second holding device, and an activation device configured to move the switch device between the first operating position and the second operating position. The activation device includes a spring and a release device.

16 Claims, 5 Drawing Sheets (52) U.S. Cl.
CPC .... *A61B 17/0625* (2013.01); *A61B 17/06066* (2013.01); *A61B 2017/0472* (2013.01); *A61B 2017/0609* (2013.01); *A61B 2017/06019* (2013.01)

(58) Field of Classification Search
CPC .. A61B 2017/0472; A61B 2017/06019; A61B 2017/0609
See application file for complete search history.

(56) References Cited

U.S. PATENT DOCUMENTS

| | | | |
|---|---|---|---|
| 5,728,113 A * | 3/1998 | Sherts | A61B 17/0469 112/169 |
| 5,876,412 A * | 3/1999 | Piraka | A61B 17/062 606/139 |
| 2014/0257345 A1 * | 9/2014 | Holwerda | A61B 17/2909 606/145 |
| 2014/0276988 A1 | 9/2014 | Tagge et al. | |

* cited by examiner

SURGICAL SUTURE APPARATUS

CROSS-REFERENCE TO RELATED APPLICATIONS

This application is the National Stage of International Application No. PCT/NL2017/050152, filed Mar. 10, 2017, which claims the benefit of Netherlands Application No. NL 2016418, filed Mar. 11, 2016, the contents of which is incorporated by reference herein.

FIELD OF THE INVENTION

The present invention relates to a surgical suture apparatus. The present invention in particular relates to a surgical suture apparatus for passing a double-ended surgical needle forwards and backwards for suturing.

BACKGROUND OF THE INVENTION

Such surgical apparatus is for example known from WO 2013/032329, the contents of which are herein incorporated by reference, in its entirety. This known surgical apparatus comprises a first jaw element, comprising a first holding device to hold a first needle-end of the surgical needle, and a second jaw element comprising a second holding device to hold a second needle-end of the surgical needle.

An operating device is provided, to operate the first holding device and the second holding device to alternately hold the first needle-end by the first holding device and the second needle-end by the second holding device.

The first jaw element and the second jaw element are movable with respect to each other between a take-over position, wherein a surgical needle can be passed between the first holding device and the second holding device, and an open position, wherein the first holding device and the second holding device are spaced further from each other.

The surgical apparatus comprises one or more first spring elements to bias the first jaw element and the second jaw element to the open position with a first biasing force. The operating device of the surgical apparatus of WO 2013/032329 comprises an operating element movable between a normal position and a depressed position, the first operating element being biased to the normal position by one or more second spring elements with a second biasing force.

The first biasing force is smaller than the second biasing force such that exerting an actuation force on the first operating element first results in movement of the first jaw element and the second jaw element towards each other, and subsequently in activation of the operating device.

The drawback of the suturing apparatus of WO 2013/032329, is that the depression of the first operating element to activate the activation device is relatively small. Therefore, there is only a small stroke of the first operating element available, in order to reliably activate the operating device to operate the first holding device and/or the second holding device.

Such small stroke provides a relative low amount of energy to operate the operating device. As a result, it may be difficult to provide an operating device which reliably operates the first holding device and the second holding device. At the same time, it is undesirable to substantially increase the stroke of the first operating element and/or to substantially increase the force required to depress the operating element.

It is an aim of the present invention, to provide an surgical suture apparatus of the above-mentioned type having an operating device which allows a reliable operation of the first holding device and the second holding device, while at the same time having an acceptable stroke and associated force to operate the operating device.

More generally, it is an aim of the present invention to provide an improved surgical suture apparatus.

The present invention provides a surgical apparatus as described herein below.

In accordance with the invention, the operating device comprises a switch device movable, for example tiltable, between a first operating position, in which a needle is held by the first holding device, and a second operating position, in which the needle is held by the second holding device, and an activation device configured to move the switch device between the first operating position and the second operating position, wherein the activation device comprises a spring and a release device, wherein the spring is configured to be pre-tensioned during movement of the first jaw element and the second jaw element from the open position to the take-over position, and wherein the release device is configured to release, upon activation, the pre-tensioned spring to move the switch device between the first operating position and the second operating position.

The advantage of this embodiment of the operating device, is that the movement of the first jaw element and the second jaw element towards each other, from the open position to the take-over position, is used for pre-tensioning of a spring. The potential energy that is stored in the spring during this movement can be used to activate the switch device to move between the first operating position and the second operating position, i.e. from the first operating position to the second operating position or from the second operating position to the first operating position.

The release device is provided to release, upon activation, the potential energy stored in the spring during pre-tensioning of the spring. Since the pre-tensioning takes place during movement of the first jaw element and the second jaw element, from the open position to the take-over position, the potential energy stored in the spring is already available when the first jaw element and the second jaw element are brought in the take-over position.

The potential energy stored in the spring may be substantially larger than the energy that is obtained by the depression of an operating element after the first jaw element and the second jaw element have been moved to the take-over position. Thereby, the potential energy may be used in combination with further energy obtained during activation of the operating device.

It is remarked, that the spring may be any element that is capable of converting mechanical energy, provided by the movement of the first jaw element and the second jaw element, from the open position to the take-over position, into potential energy.

The spring may for example comprise at least one spring element, such as a helical spring or a leaf spring, but also an element of elastic material, such as a rubber or rubber-like material. The spring may also comprise an air chamber, for example formed by a piston and a cylinder.

In an embodiment, the surgical apparatus comprises a main body, wherein the first jaw element and the second jaw element are movably connected to the main body, and wherein the operating device is arranged in the main body.

In an embodiment, the first jaw element and the second jaw element are configured to be, in an activation movement, at least partly moved from the take-over position towards each other, and wherein the release device is configured to be released by the activation movement. At the end of the movement of the first jaw element and the second jaw element, from the open position to the take-over position, potential energy is stored in the spring. To release this potential energy, a release device is provided that is configured to release, upon activation, the spring in order to move the switch device between the first operating position and the second operating position. The activation movement to activate the release device can be provided by a further movement of at least a part of the first jaw element and the second jaw element towards each other.

The activation movement of the first jaw element and the second jaw element from the take-over position towards each other takes in particular place at the parts of the first jaw element and the second jaw element, where the operating surfaces or operating elements are provided to exert a pinching force on the first jaw element and the second jaw element. These operating surfaces or operating elements are preferably provided in a middle part of the first jaw element and the second jaw element, i.e. between the distal end and the proximal end of the first jaw element and the second jaw element, respectively.

At the beginning of the activation movement, the first jaw element and the second jaw element are in the take-over position, in which the needle-ends of the needle are placed in the first holding device and the second holding device.

Therefore, the first jaw element and the second jaw element may be configured to rotate about the respective needle-ends arranged in the first holding device and the second holding device during the activation movement of the first jaw element and the second jaw element.

To allow the first jaw element and the second element to rotate about the respective needle-ends, the first jaw element and/or the second jaw element are configured to be bendable. By bending of the first jaw element and/or the second jaw element, the first jaw element and the second jaw element can be moved towards each other in a middle part thereof, while the proximal ends and the distal ends of the first jaw element and the second jaw element remain substantially in the same position.

The bendability of the first jaw element and/or second jaw element may be obtained by providing a bendable material and/or structure. For example, the first jaw element and/or second jaw element may have flexible parts, for example thinned parts, that facilitate bending of the respective jaw element. Any other arrangement to make movement of the first jaw element and second jaw element from the take-over position towards each other may also be applied.

It is remarked that the invention also provides a surgical suture apparatus for passing a double-ended surgical needle forwards and backwards, wherein the first jaw element and the second jaw element are configured to be, in an activation movement, at least partially moved from the take-over position towards each other, and wherein the operating device is configured to be operated by the activation movement. In such apparatus, the first jaw element and the second jaw element may be configured to rotate about the respective needle-ends arranged in the first holding device and the second holding device during the activation movement of the first jaw element and the second jaw element.

In an alternative embodiment, activation of the activation device may be carried out by using one or more operating elements, for example operating buttons that are movable with respect to the first jaw element and/or second jaw element.

In an embodiment, the activation device comprises:
a movable hammer configured to switch the switch device between the first operating position and the second operating position by movement of the hammer from a start position to an activation position,
wherein the spring, when pre-tensioned, is arranged to push the hammer element towards the activation position,
wherein the release device is movable between a blocking position, in which the release device blocks movement of the hammer towards the activation position, and a release position, in which the hammer can freely move from the start position towards the activation position, wherein the release device is biased in the blocking position, and
wherein, upon activation, the release device is moved from the blocking position to the release position to release the hammer to move towards the activation position.

To move the switch device between the first operating position and the second operating position, a movable hammer may be provided that is moved towards an activation position to activate the switch device. The potential energy that is stored in the spring may be used to move the hammer towards the activation position.

In order to prevent the hammer from moving towards the activation position before the activation device is activated, a release device is provided which is movable between a blocking position and a releasing position. In the blocking position, the release device prevents the hammer from moving towards the switch device. Thus, when the release device is in the blocking position, the spring may be pre-tensioned by pushing against an end of the spring faced away from the hammer, for example by moving a spring compression device positioned at the end of the spring faced away from the hammer, towards the hammer.

During activation, for example an activation movement of at least a part of the first jaw element and the second jaw element, from the take-over position towards each other, the release device may be moved to the release position, in which the pre-tensioned spring is released by the release device. As a result, the hammer will move to the activation position to move the switch element from the first operating position to the second operating position or from the second operating position to the first operating position.

In an embodiment, the spring is a helical spring and the activation device comprises a spring compression element to compress the spring when the first jaw element and the second jaw element are moved towards each other, from the open position to the take-over position.

In an embodiment, the spring compression element is configured to move the release device from the blocking position to the release position. The spring compression element is moved in longitudinal direction of the apparatus to compress the spring between the spring compression element and the hammer to pre-tension the spring. When the spring is sufficiently compressed and the first jaw element and the second jaw element are in the take-over position, the spring compression element may also be used to actuate the release device in order to release the spring.

In an embodiment, the activation device comprises a first connection element rotatably connected to the first jaw element and to the spring compression element, and a second connection element rotatably connected to the second jaw element and to the spring compression element, wherein the first connection element and the second connection element are configured to transfer an activation movement of the first jaw element and the second jaw element to the spring compression element.

To activate the switch device, the first jaw element and the second jaw element are moved towards each other. To transfer this movement into a movement of the spring compression element, the spring compression element may be connected to the first jaw element with a first connection element and to the second jaw element with a second connection element.

Due to the first connection element and the second connection element, the activation movement of the first jaw element and the second jaw element towards each other is converted into a movement of the spring compression element, most likely parallel to the first jaw element and the second jaw element. The first connection element and the second connection element may also align the first jaw element and the second jaw element with respect to each other.

In an embodiment, the activation device comprises a pusher element to cooperate with the switch device, and wherein the switch device comprises a first cam profile and a second cam profile, wherein the first cam profile is configured to cooperate with the pusher element to move the switch device from the first operating position to the second operating position, and wherein the second cam profile is configured to cooperate with the pusher element to move the switch device from the second operating position to the first operating position.

The use of a first cam profile and a second cam profile on the switch device, to switch the switch device between the first operation position and the second operating position, provides a reliable switching of the switch device. The pusher element is provided to alternately follow the shape of the first cam profile and the second cam profile. The pusher element may, for example, be mounted on a hammer configured to be moved, upon release by the release device, from a start position to an activation position, to activate the switch device.

In an embodiment, the release device comprises a tiltable lever element, which is tiltable between the release position and the blocking position. The lever element may be configured to be at least partially plastically deformed during assembly, in order to adapt the shape of the lever element during assembly to compensate for play or tolerances in other parts of the apparatus, in particular the activation device. When the parts of the operating device are put together, there may be some play or tolerance in the operating device, that may influence proper functioning of the operating device. By providing the plastically deformable lever element, this play or tolerance can be substantially reduced in a simple and reliable manner by adapting the shape of the lever element.

In particular, as one of the final steps of the assembly of the apparatus, one end of the lever element may be held in a fixed position during activation of the activation device, resulting in an activation force being exerted on the lever element. This activation force can be used to plastically deform the lever element to a suitable shape to ensure that any play or tolerance within the chain of parts forming the operating device will be sufficiently compensated for proper functioning of the operating device.

In an embodiment, the first holding device and the second holding device each comprise a needle channel to receive a respective needle-end and a needle locking element to lock the needle-end in the needle channel, wherein the needle locking element is movable between a non-locking position and a locking position, wherein the needle locking element is biased by a biasing element in the locking position.

The advantage of such first and second holding device is that the needle-end can only be moved out of the respective holding device, when the needle locking element is actively pulled out of the needle channel against the biasing force of the biasing element, for example a spring. It is remarked that such needle locking element that is biased by a biasing element into the locking position to lock the needle-end in the needle channel, may also be applied in a surgical apparatus for passing a double-ended surgical needle forwards and backwards without the switch device and the activation device features described herein.

In an embodiment, the switch device is configured to pull, in the first operating position, the needle locking element of the second holding device against a biasing force of the biasing element into the non-locking position, and wherein the switch device is configured to pull, in the second operating position, the needle locking element of the first holding device against a biasing force of the biasing element into the non-locking position. In such embodiment, switching the position of the switch device between the first operating position and the second operating position results in changing the needle locking element on which a pulling force is exerted.

In an embodiment, the apparatus comprises at least one needle release element configured to manually move the needle locking element of the first holding device and/or the needle locking element of the second holding device into the non-locking position, while the first jaw element and the second jaw element are in the open position, to allow removal of the needle out of the apparatus. Such at least one needle release element can be used to release the needle from the apparatus when suturing has been finished and/or when exchange of a needle is desired.

In such embodiment, the least one needle release element may for example be configured to manually move the switch device from the first operating position to the second operating position and/or from the second operating position to the first operating position, while the first jaw element and the second jaw element are in the open position. Preferably, there is a first needle release element to move the switch device from the first operating position to the second operating position and a second needle release element to move the switch device from the second operating position to the first operating position In an alternative embodiment, the at least one needle release element may be configured to manually pull back the needle locking element of the first holding device and/or the second holding device into the non-locking position.

In order to ensure safe operation of the apparatus, it should be ensured that the at least one needle release element is configured and/or shaped such that inadvertent operation, for example depression, of the at least one needle release element is prevented.

In an embodiment, the apparatus comprises an elongate first lock control element, which connects the switch device with the needle locking element of the first holding device and which is slidably arranged in a channel arranged in the first jaw element, and the apparatus comprises an elongate second lock control element, which connects the switch device with the needle locking element of the second holding device and which is slidably arranged in a channel arranged in the second jaw element.

These first lock control element and second lock control element provide a simple and reliable connection between the switch device and the respective needle lock elements in order to operate the first holding device and the second holding device by movement of the switch device between the first operating position and the second operating position.

BRIEF DESCRIPTION OF THE DRAWINGS

Further characteristics and features of embodiments of the invention will be described hereinafter, whereby reference will be made to the accompanying drawings, in which.

DETAILED DESCRIPTION OF THE INVENTION

Figure 1:
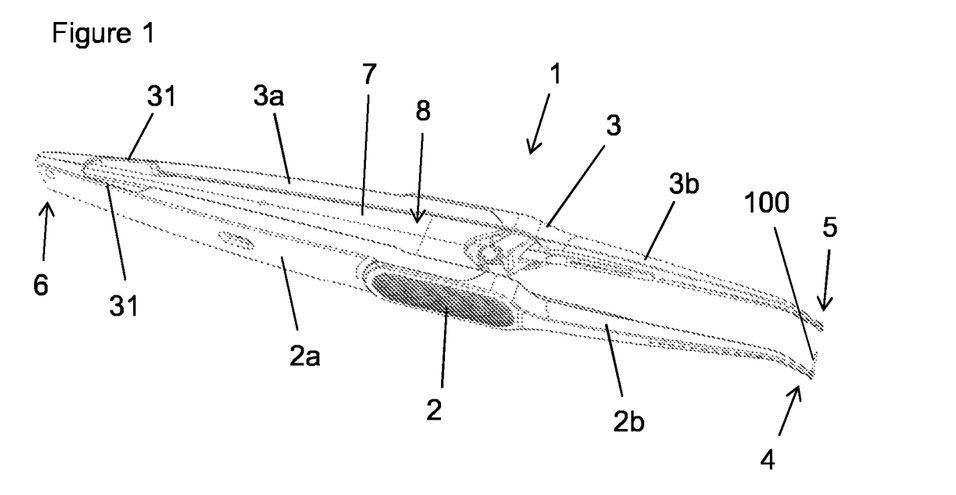
FIG. 1 shows a perspective view of an embodiment of a surgical apparatus according to the invention.

FIG. 1 shows schematically an embodiment of a surgical apparatus of the invention. The surgical apparatus is generally indicated by reference numeral 1.

The surgical apparatus 1 comprises a first jaw element 2 and a second jaw element 3. The first jaw element 2 comprises a first holding device 4 configured to hold a needle-end of a double-ended needle 100, and the second jaw element 3 comprises a second holding device 5 configured to hold an opposite needle-end of the needle 100.

The surgical apparatus 1 is configured to pass a double-ended surgical needle 100 forwards and backwards so that the surgical apparatus can be used to apply sutures to human or animal body tissue. The surgical apparatus 1 may be made of any suitable material such as a (non-toxic and/or biocompatible) plastic or metal, or combinations thereof.

The proximal ends of the first jaw element 2 and the second jaw element 3 are connected to each other at a distal end 6 of the apparatus The first jaw element 2 and the second jaw element 3 are movable with respect to each other between a take-over position, in which the surgical needle 100 can be taken over between the first holding device 4 and the second holding device 5, and an open position, in which the first holding device 4 and the second holding device 5 are spaced further from each other. In FIG. 1, the surgical apparatus 1 is shown in the open position. In this open position, body tissue can be placed between the needle 100 and the one of the first jaw element 2 and the second jaw element 3 that does not hold the needle 100.

Between the first jaw element 2 and the second jaw element 3, a main body 7 of the surgical apparatus is provided. In this main body 7, an operating device 8 is arranged, which operating device 8 is configured to operate the first holding device 4 and the second holding device 5, to alternately hold a needle-end of the needle 100 by the first holding device 4 and the second needle-end by the second holding device 5.

Figure 2:
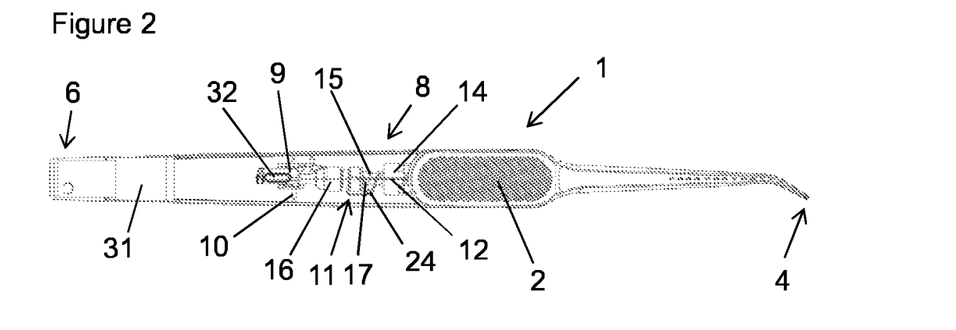
FIG. 2 shows a side view of FIG. 1 without a part of the first jaw element being shown.
Figure 3:
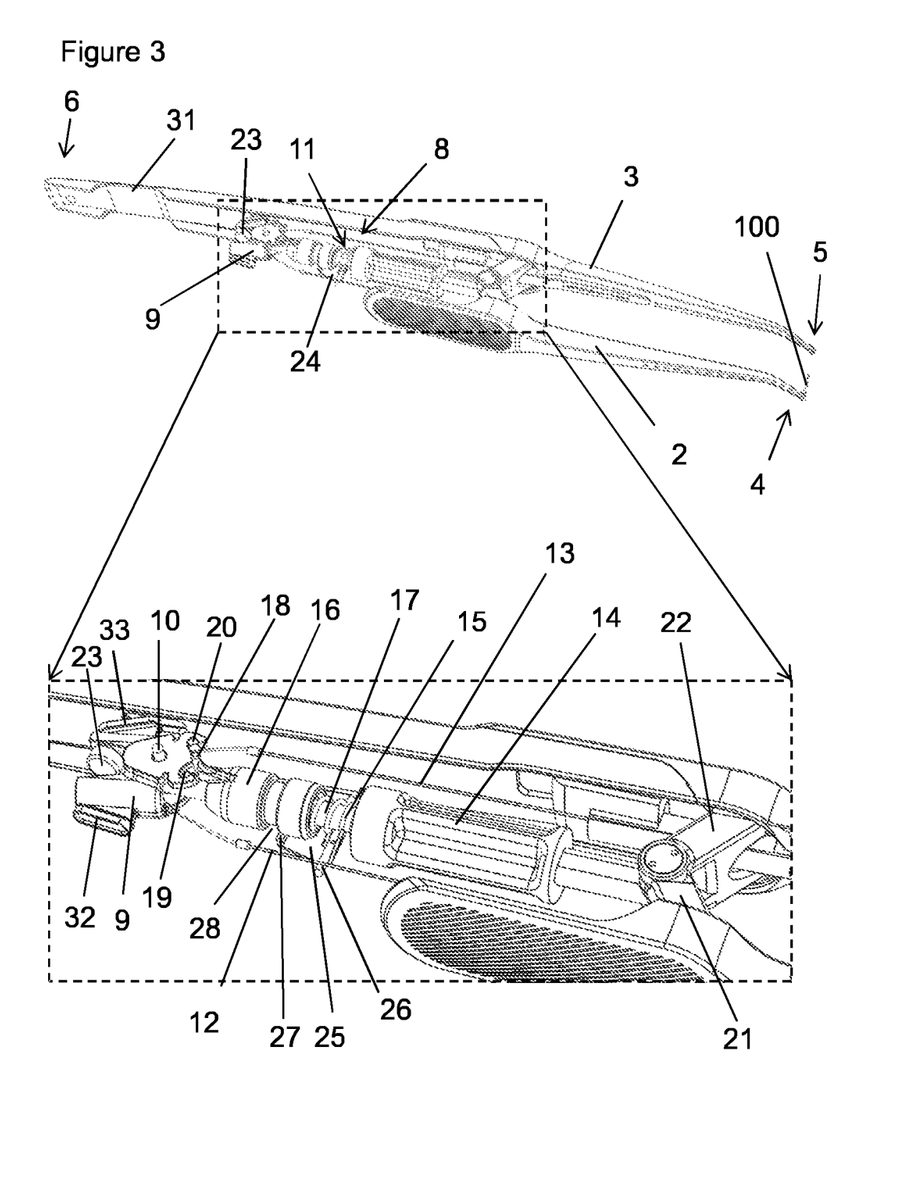
FIG. 3 shows a perspective view of the embodiment shown in FIG. 2.

In FIGS. 2 and 3, the operating device 8 is shown in more detail. To obtain a view into the interior of the main body 7, the housing part of the main body 8 and a distal part 2a of the first jaw element 2 are not shown in FIGS. 2 and 3.

The operating device 8 comprises a switch device 9 which is tiltable about a switch axis 10 between a first operating position and a second operating position. The operating device 8 further comprises an activation device 11 configured to move the switch device 9 between the first operating position and the second operating position.

When the switch device 9 is in the first operating position, as shown in FIG. 1, the first holding device 4 holds and locks the needle 100, while the second holding device 5 allows free movement of a needle-end into and out of the second holding device 5. By activation of the activation device 11, the switch device 9 may be tilted about switch axis 10 to the second operating position. In the second operating position, the needle is locked by the second holding device 5 and no longer locked by the first holding device 4.

To operate the first holding device 4, the switch device 9 is connected to a first lock control element 12 and to operate the second holding device 5, the switch device 9 is connected to a second lock control element 13. As will be explained hereinafter, with respect to FIGS. 6a and 6b, the needle-end of a needle 100 placed in the first holding device 4 or the second holding device 5 may be unlocked by pulling the first lock control element 12 or the second lock control element 13 in a distal direction (to the rear end of the apparatus), respectively. However any other suitable embodiment of a first holding device and a second holding device operable by the operating device 8 may also be applied.

The activation device 11 shown in FIGS. 2 and 3, comprises a spring compression element 14, a spring 15 and a hammer 16. The spring compression element 14, the spring 15 and the hammer 16 are movable in a longitudinal direction of the apparatus 1. At a distal side of the spring compression element 14, a cylindrical extension 17 extends from the spring compression element 14. The hammer 16 comprises a longitudinal channel through which the cylindrical extension 17 is arranged. The spring 15 is a helical spring arranged around the cylindrical extension 17, and between the spring compression element 14 and the hammer 16.

The hammer 16 comprises a pusher element 18 configured to cooperate with a first cam profile 19 and a second cam profile 20 on the switch device 9. When the hammer 16 is moved from a start position shown in FIGS. 2 and 3 towards an activation position in a distal direction of the apparatus 1, the pusher element 18 will be moved into the first cam profile 19. This first cam profile 19 is shaped to move the switch device 9 to the second operating position, when the pusher element 18 is pushed into this first cam profile 19.

Correspondingly, when the hammer 16 is moved from the start position, when the switch device 9 is in the second operation position, towards an activation position in a distal direction of the apparatus 1, the pusher element 18 will be moved into the second cam profile 20. This second cam profile 20 is shaped to move the switch device 9 from the second operating position to the first operating position, when the pusher element 18 is pushed into this second cam profile 20.

It is remarked that the hammer 16 is arranged rotatable on the cylindrical extension 17 to allow the pusher element 18 to follow the first cam profile 19 and the second cam profile 20 during a movement of hammer 16 from a start position to an activation position.

The spring compression element 14 is rotatably connected to a first end of a first connection element 21 while the other end of the first connection element 21 is rotatably connected to the first jaw element 2. The spring connection element 14 is also rotatably connected to a first end of a second connection element 22 and the other end of the second connection element 22 is rotatably connected to the second jaw element 3.

Movement of the first jaw element 2 and the second jaw element 3 towards each other will, due to the first connection element 21 and the second connection element 22, result in a movement of the spring compression element 14 in a distal direction of the apparatus 1.

To ensure that the switch device 9 remains either in the first operating position or in the second operating position as long as the activation device 11 is not activated to switch the switch device 9 between the first operating position and the second operating position, a magnetic element 23 is provided at a fixed position, i.e. the magnetic element 23 does not move together with the switch device 9. The magnetic element 23 comprises a permanent magnet and is configured to cooperate with magnetic parts of the switch device 9 to hold the switch device 9 in the first operating position or second operating position, respectively. Any other device or construction to hold the switch device 9 either in the first operating position or in the second operating position, as long as the activation device 11 is not activated may also be used.

The operating device 8 further comprises a release device 24 having a tiltable lever element 25 which is tiltable about a lever element axis 26 between a blocking position and a release position. In FIGS. 2 and 3 the release device 24 is shown in the blocking position. In this blocking position a hook-end 27 of the lever element 25 is hooked in a groove 28 of the hammer so that movement of the hammer 16 towards the activation position is blocked by the lever element 25. To ensure that the lever element 25 will not move out of the blocking position, the lever element 25 is biased into the blocking position. The lever element 25 can be pushed from the blocking position to the release position by pushing the spring compression element 14 against lever element 25.

Since the hammer 16 is held by the release device 24 in the start position, shown in FIGS. 2 and 3, the movement of the spring compression element 14 in a distal direction of the apparatus, will first compress the spring 15 between the spring compression element 14 and the hammer 16, before the hammer 16 is released by the release device 24. This compression of the spring 15, which takes place while moving the first jaw element 2 and the second jaw element from the open position to the take-over position, stores potential energy in the spring 15. The operating device 8 is configured to use this potential energy for switching the switch device 9.

It is remarked that the lever element 25 is configured to be at least partially plastically deformed during assembly of the apparatus 1 to adapt the shape of the lever element 25 to compensate for play or tolerances in other parts of the apparatus, in particular the operating device 8. This plastic deformation of the lever element 25 is used as follows.

In one of the final steps of the assembly of the apparatus 1, when the different parts of the apparatus 1 are already put together, the hook end 27 of the lever element 25 can be held in a fixed position, while the first jaw element 2 and the second jaw element 3 are pushed towards each other to activate the activation device 11. Since the hook end 27 is held in a fixed position, the pushing movement of the spring compression element 14 against the lever element 25 will result in a plastic deformation of the lever element 25, in particular a change of the angle of the first lever element arm comprising the hook end 27 with respect to the second lever element arm which is in contact with the spring compression element 14.

This plastic deformation, in particular the adapted angle of the first lever element arm and the second lever element arm, results in that the activation device 11 can be optimally configured for timely release of the hammer 16 without having very stringent requirements for each part of the activation device 11 during production. The plastically deformable lever element 25 therewith provides a simple and reliable way of compensating play and tolerances in the apparatus, The operation of the surgical apparatus 1 will now be described.

Figures 4A, 4B:
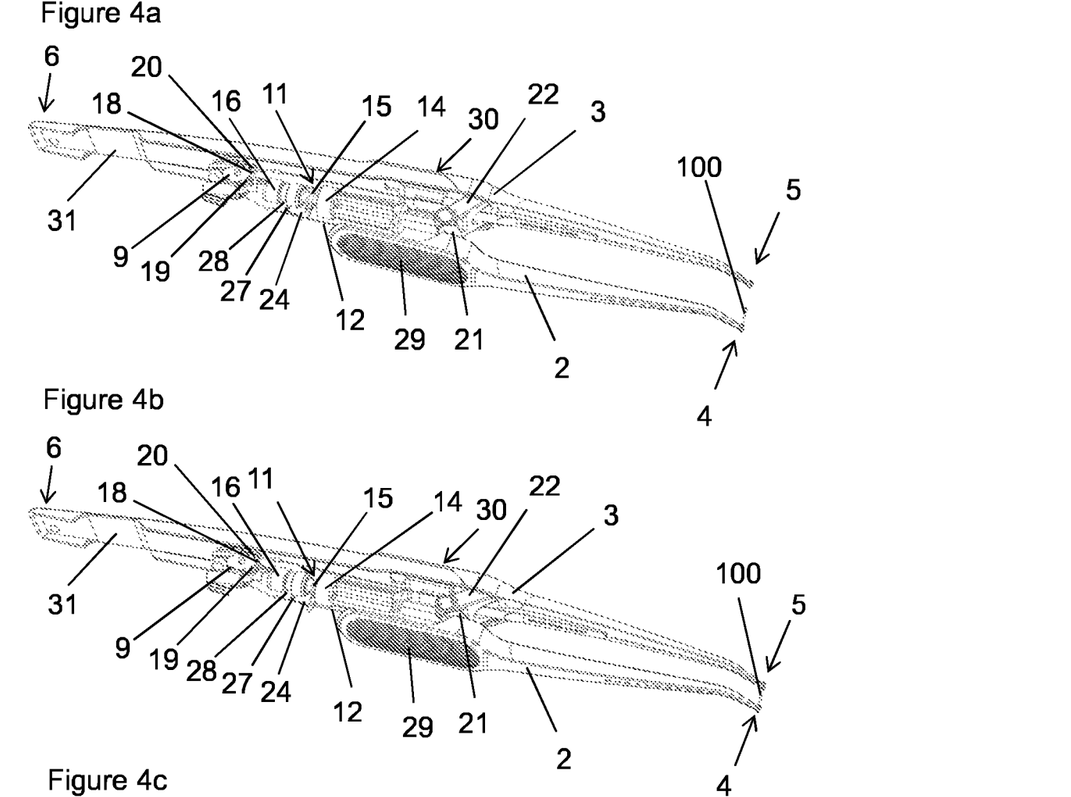
FIGS. 4a, 4b and 4c show perspective views corresponding to the perspective view of FIG. 3 in different positions during handling of the operating device.
Figure 5A:
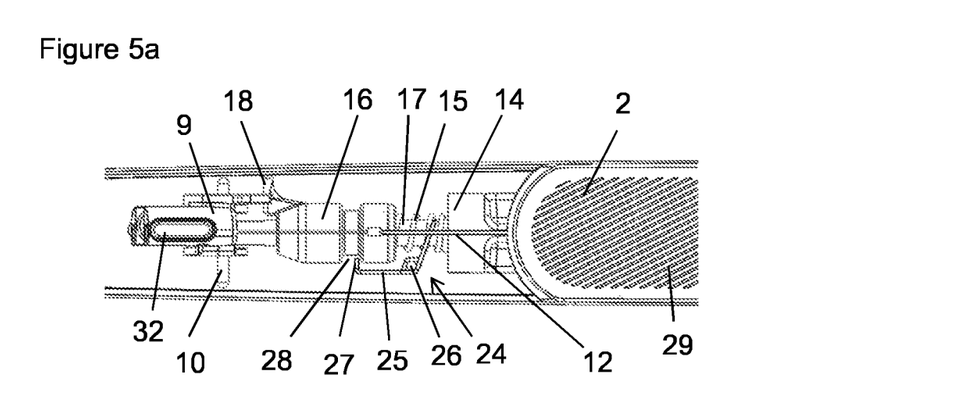
FIGS. 5a, 5b and 5c show side views corresponding to a detail of the side view of FIG. 2 in different positions during handling of the operating device.

FIGS. 4a and 5a show the apparatus 1 in the normal, non-actuated state of the apparatus, similar views to FIGS. 3 and 2, respectively. The first jaw element 2 and the second jaw element 3 are arranged in the open position. A first needle-end of the needle 100 is held by the first holding device 4 and the second holding device 5 is spaced from the opposite second needle-end. In this non-actuated position of the apparatus, the needle 100 can be pierced through body tissue to place a suture using a suture attached to the needle 100.

When the needle 100 is correctly placed in the tissue, the first jaw element 2 and the second jaw element 3 may be moved from the open position to the take-over position, by exerting a pinching force, for example with a thumb and a finger on a first operating surface 29 on the first jaw element 2 and a second operating surface 30 on the second jaw element 3, respectively. In the take-over position, the first needle-end is still held by the first holding device 4, and the second needle-end is now arranged in the second holding device 5.

Figure 5B:
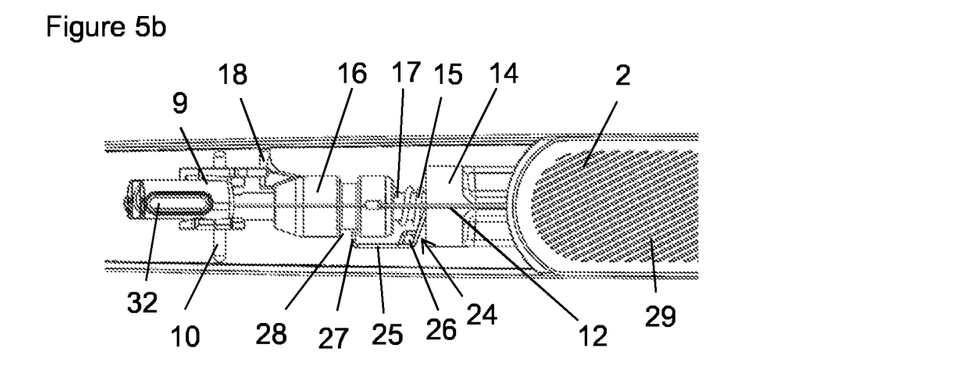

FIGS. 4b and 5b show the apparatus 1, when the first jaw element 2 and the second jaw element 3 are almost in the take-over position. Due to the movement of the first jaw element 2 and the second jaw element 3 towards each other, the spring compression element 14 is pushed by the first connection element 21 and the second connection element 22 in a distal direction, i.e. in the direction of the distal end 6 of the apparatus. At the same time, the hammer 16 is prevented by the release device 24 from a movement towards the switch device 9. As a result, the movement of the spring compression element 14 will pre-tension, in particular compress the spring 15 so that potential energy is stored in the spring 15.

When the first jaw element 2 and the second jaw element 3 are moved into the take-over position, the release device 24 is still in the blocking position and therewith prevents the hammer 16 from moving in a distal direction towards the switch device 9.

In the take-over position, it can still be checked whether the needle 100 is correctly placed in the tissue. When correction of the placement of the needle is desired the pinching force on the first operating surface 29 and the second operating surface 30 can be released, and the first jaw element 2 and the second jaw element 3 will move back to the open position. When no correction of the placement of the needle 100 is desired, the activation device 11 can be activated to move the switch device 9 from the first operating position to the second operating position in order to release the first needle-end in the first holding device 4 and simultaneously lock the second needle-end in the second holding device 5.

To activate the activation device 11, the first jaw element 2 and the second jaw element 3 can be moved in an activation movement, at least partly, from the take-over position towards each other. It is remarked that in the shown embodiment only the middle parts of the first jaw element 2 and the second jaw element 3, i.e. at the location of the first operating surface 29 and the second operating surface 30, will move towards each other during the activation movement, since the distal ends of the first jaw element 2 and the second jaw element 3 are connected to each other, and the needle 100 prevents further movement of the proximal ends of the first jaw element 2 and the second jaw element 3 towards each other.

This means that the needle 100 is used, during the activation movement, as a hinge for rotation of the first jaw element 2 and the second jaw element 3. Furthermore, the activation movement requires bending of the first jaw element 2 and the second jaw element 3 in order to move the first operating surface 29 and the second operating surface 30 towards each other. To facilitate bending of the first jaw element 2 and the second jaw element 3, the first jaw element 2 and the second jaw element 3 are provided with flexible portions 31 (see FIG. 1) near the distal end 6 of the apparatus 1, but the first jaw element 2 and the second jaw element 3 are also configured to bend over other parts of their extension to allow the first operating surface 29 and the second operating surface 30 to move from the take-over position towards each other.

During the activation movement, the spring compression element 14 will be moved by the first connection element 21 and the second connection element 22 further in a distal direction, and will be pushed against the lever element 25 of the release device 24 such that the lever element 25 will tilt about the lever element axis 26 from the blocking position to the release position.

In this release position, the hook-end 27 of the lever element 25 is no longer arranged in the groove 28 of the hammer 16, and the hammer 16 is free to move from its start position in a distal direction to an activation position. The potential energy stored in the spring 15 during the movement of the first jaw element 2 and the second jaw element 3, from the open position to the take-over position, is now used to push the hammer 16 towards the activation position. During this movement of the hammer 16, the pusher element 18 of the hammer 16 will be moved along the first cam profile 19, which will result in a movement of the switch device 9, from the first operating position to the second operating position.

Figure 4C:
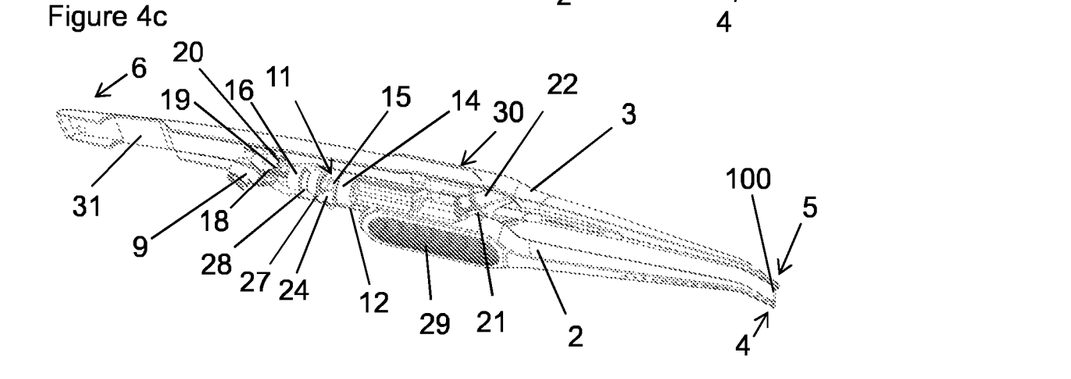
Figure 5C:
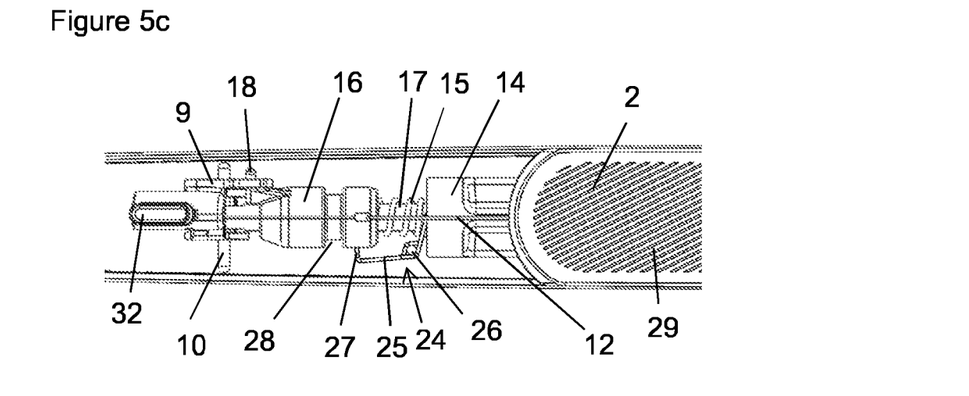

FIGS. 4c and 5c show the apparatus 1 after the hammer 16 has pushed with the pusher element 18 the switch device 9 to the second operating position. The first lock control element 12 is now pulled backwards so that the first needle-end of needle 100 is no longer locked in the first holding device 4, while the second lock control element 13 is no longer pulled backwards so that the second needle-end of needle 100 is locked in the second holding device 5.

When the first jaw element 2 and the second jaw element 3 are released, the first jaw element 2 and the second jaw element 3 will move back to the open position as shown in FIGS. 4a and 5a, but the needle is now held by the second holding device 5. During the movement back to the open position, the activation device 11 will also return to the start position shown in FIGS. 4a and 5a, but the pusher element 18 of the hammer 16 will now be aligned with the second cam profile 20.

When the first jaw element 2 and the second jaw element 3 are now again moved from the open position to the take-over position, and subsequently at least partly further towards each other in the activation movement, the activation device 11 will again activate the movement of the switch device 9, but now from the second operating position to the first operating position by pushing the pusher element 18 against the second cam profile 20.

It will be clear that by subsequent further actuation of the apparatus 1, the needle can be passed forwards and backwards between the first holding device 4 and the second holding device 5 to apply a suture through the tissue.

Once a needle 100 is arranged in the apparatus 1, it will be held by one of the first holding device 4 and the second holding device 5. To release the needle 100 from the apparatus, the switch device comprises a first needle release element 32, configured to manually move the switch device 9 from the first operating position to the second operating position, and a second needle release element 33, configured to manually move the switch device 9 from the second operating position to the first operating, while the first jaw element 2 and the second jaw element 3 are in the open position. Openings are provided in the first jaw element 2 and the second jaw element 3 to provide access to the first needle release element 32 and the second needle release element 33, respectively.

Figure 6A:
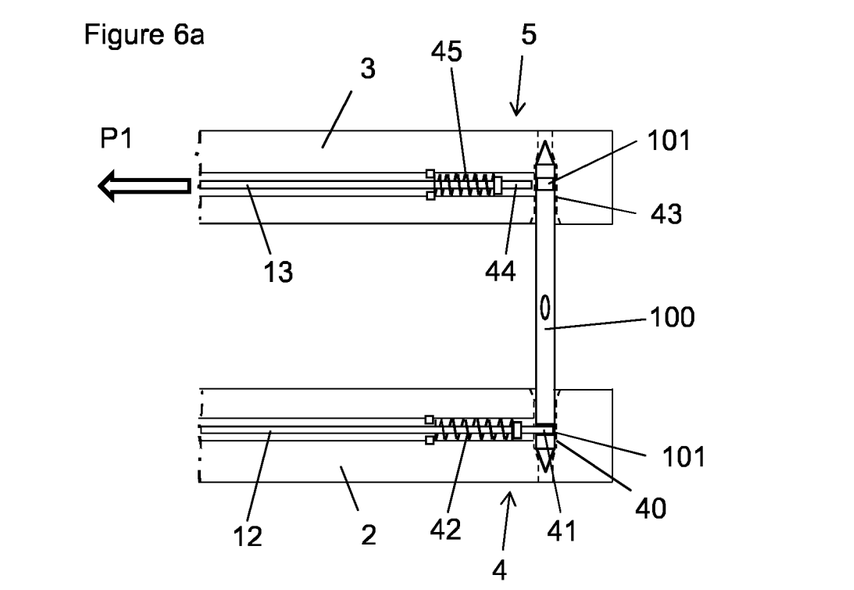
FIGS. 6a and 6b shows a detail of the first and second holding device holding a needle.

FIG. 6a shows schematically the first holding device 4 and the second holding device 5, when the switch device 9 is in the first operation position and the first jaw element 2 and the second jaw element 3 are in the take-over position.

The first holding device 4 comprises a needle channel 40 to receive a first needle-end of the needle 100, and a needle locking element 41 configured to lock the needle 100 in the needle channel 40. The needle locking element 41 is movable between a non-locking position and a locking position. In the locking position, the needle locking element 41 extends into the needle channel 40 and into a groove 101 provided at a side of the needle-end of the needle 100 to prevent that the needle 100 can be pulled out of the needle channel 40. In the non-locking position the needle locking element 41 does not extend into the needle channel 40, and the needle can freely be moved into and out of the needle channel 40.

In FIG. 6a, the needle locking element 41 is biased into the locking position by a biasing element formed by a lock spring 42. By exerting a pulling force on the lock control element 12 exceeding the lock spring force of lock spring 42, the needle locking element 41 can be moved from the locking position to the non-locking position to allow the needle-end to be moved out of the needle channel 40.

Similarly, the second holding device 5 comprises a needle channel 43 to receive the second needle-end of the needle 100, and a needle locking element 44 configured to lock the needle 100 in the needle channel 43. The needle locking element 44 is movable between a non-locking position and a locking position, and biased by a lock spring 45 to the locking position. However, the pulling force P1 exerted on the lock control element 13 and exceeding the lock spring force of lock spring 45, has moved the needle locking element 44 out of the locking position into the non-locking position to allow the needle-end to be moved out of the needle channel 43.

Figure 6B:
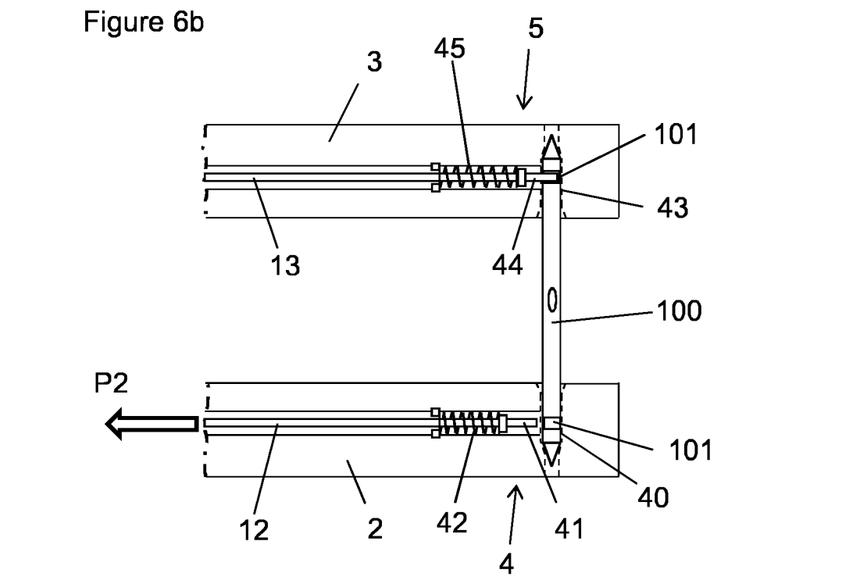

FIG. 6b shows schematically the first holding device 4 and the second holding device 5, when the switch device 9 is in the second operation position and the first jaw element 2 and the second jaw element 3 are in the take-over position.

Since the switch device 9 is now switched to the second operating position, the needle 100 is held by the second holding device 5, since the pulling force P1 is no longer exerted on the lock control element 13. As a result, the lock spring 45 pushes the needle locking element 44 into the needle channel 43 and into the groove 101 provided in the first needle-end of the needle 100 and locks the needle in the needle channel 43 of the second holding device 5.

The needle locking element 44 is pulled by a pulling force P2 exerted by the switch device 9 on the lock control element 12 against the biasing force of the spring 42 out of the needle channel 40. The needle 100 can therefore be freely moved out of the needle channel 40 of the first holding device 4.

1 surgical apparatus
2 first jaw element
2a distal part of first jaw element
2b proximal part of first jaw element
3 second jaw element
3a distal part of second jaw element
3b proximal part of second jaw element
4 first holding device
5 second holding device
6 distal end of the apparatus
7 main body
8 operating device
9 switch device
10 switch axis
11 activation device
12 first lock control element
13 second lock control element
14 spring compression element
15 spring
16 hammer
17 cylindrical extension
18 pusher element
19 first cam profile
20 second cam profile
21 first connection element
22 second connection element
23 magnetic element
24 release device
25 lever element
26 lever element axis
27 hook end of lever element
28 groove (in hammer)
29 first operating surface
30 second operating surface
31 flexible portion
32 first needle release element
33 second needle release element
40 needle channel of first holding device
41 needle locking element of first holding device
42 lock spring of first holding device
43 needle channel of second holding device
44 needle locking element of second holding device
45 lock spring of second holding device

The invention claimed is:

1. A surgical suture apparatus for passing a double-ended surgical needle forwards and backwards, wherein the surgical apparatus comprises:
a first jaw element, comprising a first holding device to hold a first needle-end of the surgical needle,
a second jaw element comprising a second holding device to hold a second needle-end of the surgical needle,
an operating device to operate the first holding device and the second holding device to alternately hold the first needle-end by the first holding device and the second needle-end by the second holding device, and
wherein the first jaw element and second jaw element are movable with respect to each other between a take-over position, wherein a surgical needle can be passed between the first holding device and the second holding device, and an open position, wherein the first holding device and the second holding device are spaced further from each other,
wherein the operating device comprises:
a switch device movable between a first operating position, in which a needle is held by the first holding device, and a second operating position, in which the needle is held by the second holding device, and
an activation device configured to move the switch device between the first operating position and the second operating position,
wherein the activation device comprises a spring and a spring release, wherein the spring is configured to be pre-tensioned by movement of the first jaw element and second jaw element, from the open position to the take-over position, and wherein the spring release is configured to release, upon activation, the pre-tensioned spring to move the switch device between the first operating position and the second operating position.

2. The apparatus of claim 1, wherein the first jaw element and the second jaw element are configured to be, in an activation movement, at least partly moved from the take-over position towards each other, and wherein the spring release is configured to be released by the activation movement.

3. The apparatus of claim 2, wherein during the activation movement of the first jaw element and the second jaw element, the first jaw element and the second jaw element rotate about the respective needle ends arranged in the first holding device and the second holding device.

4. The apparatus of claim 3, wherein the first jaw element and/or the second jaw element are configured to be bendable in order to move the first jaw element and the second jaw element towards each other from the take-over position.

5. The apparatus of claim 1, wherein the activation device comprises:
a movable hammer configured to switch the switch device between the first operating position and the second operating position by movement of the hammer from a start position to an activation position,
wherein the spring, when pre-tensioned, is arranged to push the hammer element towards the activation position,
wherein the spring release is movable between a blocking position, in which the spring release blocks movement of the hammer towards the activation position, and a release position, in which the hammer can freely move from the start position towards the activation position, wherein the spring release is biased in the blocking position, and
wherein, upon activation, the spring release is moved from the blocking position to the release position to release the hammer to move towards the activation position.

6. The apparatus of claim 1, wherein the activation device comprises a spring compression element to compress the spring when the first jaw element and the second jaw element are moved towards each other, from the open position to the take-over position.

7. The apparatus of claim 6, wherein the spring compression element is configured to move the spring release from a blocking position to a release position.

8. The apparatus of claim 6, wherein the activation device comprises a first connection element rotatably connected to the first jaw element and to the spring compression element, and a second connection element rotatably connected to the second jaw element and to the spring compression element, wherein the first connection element and the second connection element are configured to transfer the activation movement of the first jaw element and the second jaw element to the spring compression element.

9. The apparatus of claim 1, wherein the switch device is tiltable between the first operating position and the second operating position.

10. The apparatus of claim 1, wherein the activation device comprises a pusher element to cooperate with the switch device, and wherein the switch device comprises a first cam profile and a second cam profile, wherein the first cam profile is configured to cooperate with the pusher element to move the switch device from the first operating position to the second operating position, and wherein the second cam profile is configured to cooperate with the pusher element to move the switch device from the second operating position to the first operating position.

11. The apparatus of claim 1, wherein the spring release comprises a tiltable lever element, which is tiltable between the release position and the blocking position.

12. The apparatus of claim 11, wherein the lever element is configured to be at least partially plastically deformed during assembly, in order to adapt the shape of the lever element during assembly to compensate for play or tolerances in other parts of the apparatus.

13. The apparatus of claim 1, wherein the first holding device and the second holding device each comprise a needle channel to receive a respective needle-end and a needle locking element, and
wherein each needle locking element is movable between a non-locking position in which the respective needle end freely move out of the needle channel and a locking position in which the respective needle end is locked in the needle channel, wherein each needle locking element is biased with a biasing force towards the locking position.

14. The apparatus of claim 13,
wherein the switch device is configured to pull, in the first operating position, the needle locking element of the second holding device against the biasing force into the non-locking position, and
wherein the switch device is configured to pull, in the second operating position, the needle locking element of the first holding device against the biasing force into the non-locking position.

15. The apparatus of claim 13, wherein the apparatus comprises at least one needle release, wherein the needle release is configured to move, by manual actuation, the needle locking element of the first holding device and/or the needle locking element of the second holding device into the non-locking position, while the first jaw element and the second jaw element are in the open position, to allow removal of the needle out of the apparatus.

16. The apparatus of claim 13,
wherein the apparatus comprises an elongate first lock control element, which connects the switch device with the needle locking element of the first holding device and which is slidably arranged in a channel arranged in the first jaw element, and
wherein the apparatus comprises an elongate second lock control element, which connects the switch device with the needle locking element of the second holding device and which is slidably arranged in a channel arranged in the second jaw element.

* * * * *